US00RE48907E

(19) United States
(12) Reissued Patent
DiGiore et al.

(10) Patent Number: US RE48,907 E
(45) Date of Reissued Patent: *Feb. 1, 2022

(54) SYSTEMS AND METHODS FOR MAKING AND USING IMPROVED LEADS FOR ELECTRICAL STIMULATION SYSTEMS

(71) Applicant: Boston Scientific Neuromodulation Corporation, Valencia, CA (US)

(72) Inventors: Andrew DiGiore, San Francisco, CA (US); Thomas Lopez, Sunland, CA (US)

(73) Assignee: Boston Scientific Neuromodulation Corporation, Valencia, CA (US)

( * ) Notice: This patent is subject to a terminal disclaimer.

(21) Appl. No.: 17/004,577

(22) Filed: Aug. 27, 2020

Related U.S. Patent Documents

Reissue of:
(64) Patent No.: 9,474,895
Issued: Oct. 25, 2016
Appl. No.: 14/605,781
Filed: Jan. 26, 2015

U.S. Applications:
(63) Continuation of application No. 16/165,477, filed on Oct. 19, 2018, now Pat. No. Re. 48,235, which is an application for the reissue of Pat. No. 9,474,895, which is a continuation of application No. 13/490,310, filed on Jun. 6, 2012, now Pat. No. 8,942,810.

(60) Provisional application No. 61/494,247, filed on Jun. 7, 2011.

(51) Int. Cl.
*A61N 1/05* (2006.01)
*H01B 13/00* (2006.01)
*A61N 1/08* (2006.01)

(52) U.S. Cl.
CPC ..... *A61N 1/0534* (2013.01); *H01B 13/0016* (2013.01); *Y10T 29/49117* (2015.01)

(58) Field of Classification Search
CPC ..... A61N 1/0534; H01B 13/0016
USPC ..... 607/115, 116, 122
See application file for complete search history.

(56) References Cited

U.S. PATENT DOCUMENTS 5,728,149 A 3/1998 Laske et al.
5,935,159 A 8/1999 Cross, Jr. et al.
6,249,708 B1 6/2001 Nelson et al.
(Continued)

FOREIGN PATENT DOCUMENTS

WO 2010055421 A1 5/2010
WO 2010055453 A1 5/2010

OTHER PUBLICATIONS

The International Search Report dated Aug. 16, 2012 in corresponding International Application No. PCT/US2012/041133.
(Continued)

*Primary Examiner* — Beverly M Flanagan
(74) *Attorney, Agent, or Firm* — Branch Partners PLLC; Bruce E. Black

(57) ABSTRACT

A method for manufacturing a lead includes forming an elongated multi-lumen conductor guide defining a central stylet lumen and a plurality of conductor lumens arranged around the stylet lumen. The multi-lumen conductor guide is twisted to form at least one helical section where the plurality of conductor lumens each forms a helical pathway around the stylet lumen. Each of the helical pathways of the at least one helical section has a pitch that is no less than 0.04 turns per centimeter.

20 Claims, 6 Drawing Sheets

(56) References Cited

U.S. PATENT DOCUMENTS

| | | | | |
|---|---|---|---|---|
| 6,501,991 | B1 | 12/2002 | Honeck et al. | |
| 7,047,082 | B1 | 5/2006 | Schrom et al. | |
| 7,130,700 | B2 | 10/2006 | Gardeski et al. | |
| 7,809,446 | B2 | 10/2010 | Meadows | |
| 7,824,517 | B2 | 11/2010 | Kampa et al. | |
| 8,688,235 | B1 | 4/2014 | Pianca et al. | |
| 8,942,810 | B2 * | 1/2015 | DiGiore et al. | A61N 1/0534 607/45 |
| 2007/0150036 | A1 | 6/2007 | Anderson | |
| 2008/0262584 | A1 | 10/2008 | Bottomley et al. | |
| 2009/0187222 | A1 | 7/2009 | Barker | |
| 2009/0276021 | A1 | 11/2009 | Meadows | |
| 2010/0076535 | A1 | 3/2010 | Pianca | |
| 2010/0094364 | A1 * | 4/2010 | McDonald | A61N 1/05 607/2 |
| 2010/0269339 | A1 | 10/2010 | Dye et al. | |
| 2012/0136419 | A1 | 5/2012 | Zarembo et al. | |

OTHER PUBLICATIONS

Official Communication for U.S. Appl. No. 13/490,310 dated Apr. 4, 2014.

Official Communication for U.S. Appl. No. 14/605,781 dated Sep. 21, 2015.

Official Communication for U.S. Appl. No. 14/605,781 dated Feb. 25, 2016.

Official Communication for U.S. Appl. No. 16/165,477 dated May 16, 2019.

Official Communication for U.S. Appl. No. 16/165,477 dated Oct. 3, 2019.

Official Communication for U.S. Appl. No. 16/165,477 dated Jan. 17, 2020.

The International Search Report issued on Aug. 16, 2012 in corresponding International Application No. PCT/US2012/041133.

* cited by examiner

SYSTEMS AND METHODS FOR MAKING AND USING IMPROVED LEADS FOR ELECTRICAL STIMULATION SYSTEMS

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

CROSS-REFERENCE TO RELATED APPLICATIONS

This application is a continuation of U.S. patent application Ser. No. 13/490,310 filed Jun. 6, 2012 and issued as U.S. Pat. No. 8,942,810 on Jan. 27, 2015, which claims the benefit under 35 U.S.C. § 119(e) of U.S. Provisional Patent Application Ser. No. 61/494,247 filed on Jun. 7, 2011, both of which are incorporated herein by reference.

FIELD

The invention is directed to the area of electrical stimulation systems and methods of making and using the systems. The present invention is also directed to electrical stimulation leads having leads with improved flexibility and strain relief, as well as methods of making and using the leads and electrical stimulation systems.

BACKGROUND

Electrical Stimulation can be useful for treating a variety of conditions. Deep brain stimulation can be useful for treating, for example, Parkinson's disease, dystonia, essential tremor, chronic pain, Huntington's Disease, levodopa-induced dyskinesias and rigidity, bradykinesia, epilepsy and seizures, eating disorders, and mood disorders. Typically, a lead with a stimulating electrode at or near a tip of the lead provides the stimulation to target neurons in the brain. Magnetic resonance imaging ("MRI") or computerized tomography ("CT") scans can provide a starting point for determining where the stimulating electrode should be positioned to provide the desired stimulus to the target neurons.

After the lead is implanted into a patient's brain, electrical stimulus current can be delivered through selected electrodes on the lead to stimulate target neurons in the brain. Typically, the electrodes are formed into rings disposed on a distal portion of the lead. The stimulus current projects from the ring electrodes equally in every direction. Because of the ring shape of these electrodes, the stimulus current cannot be directed to one or more specific positions around the ring electrode (e.g., on one or more sides, or points, around the lead). Consequently, undirected stimulation may result in unwanted stimulation of neighboring neural tissue, potentially resulting in undesired side effects.

BRIEF SUMMARY

In one embodiment, a method for manufacturing a lead includes forming an elongated multi-lumen conductor guide defining a central stylet lumen and a plurality of conductor lumens arranged around the stylet lumen. The multi-lumen conductor guide is twisted to form at least one helical section where the plurality of conductor lumens each forms a helical pathway around the stylet lumen. Each of the helical pathways of the at least one helical section has a pitch that is no less than 0.04 turns per centimeter. Optionally, heat is applied to the multi-lumen conductor guide to set the at least one helical section. Optionally, at least one conductor is inserted into at least one of the plurality of conductor lumens.

In another embodiment, a lead for providing deep brain stimulation includes a lead body having a distal end, a proximal end, and a longitudinal length. The lead body includes a multi-lumen conductor guide extending from the proximal end of the lead body to the distal end of the lead body. The multi-lumen conductor guide has an outer surface and defines a central stylet lumen configured and arranged for receiving a stylet and a plurality of conductor lumens disposed around the central stylet lumen. Each conductor lumen is configured and arranged to receive at least one conductor. The plurality of conductor lumens are completely inset from the outer surface of the multi-lumen conductor guide. At least a portion of the multi-lumen conductor guide is twisted such that the multi-lumen conductor guide forms at least one helical section where the plurality of conductor lumens form helical pathways around the stylet lumen. Each of the helical pathways of the at least one helical section has a pitch that is no less than 0.04 turns per centimeter. A plurality of electrodes are disposed on the distal end of the lead body. A plurality of lead terminals are disposed on the proximal end of the lead body. A plurality of conductors electrically couple at least one of the plurality of electrodes to at least one of the plurality of lead terminals. The plurality of conductors extend along the longitudinal length of the leady body within the plurality of conductor lumens.

BRIEF DESCRIPTION OF THE DRAWINGS

Non-limiting and non-exhaustive embodiments of the present invention are described with reference to the following drawings. In the drawings, like reference numerals refer to like parts throughout the various figures unless otherwise specified.

For a better understanding of the present invention, reference will be made to the following Detailed Description, which is to be read in association with the accompanying drawings, wherein.

DETAILED DESCRIPTION

The invention is directed to the area of electrical stimulation systems and methods of making and using the systems. The present invention is also directed to electrical stimulation leads having leads with improved flexibility and strain relief, as well as methods of making and using the leads and electrical stimulation systems.

A lead for deep brain stimulation may include stimulation electrodes, recording electrodes, or a combination of both. A practitioner may determine the position of the target neurons using the recording electrode(s) and then position the stimulation electrode(s) accordingly without removal of a recording lead and insertion of a stimulation lead. In some embodiments, the same electrodes can be used for both recording and stimulation. In some embodiments, separate leads can be used; one with recording electrodes which identify target neurons, and a second lead with stimulation electrodes that replaces the first after target neuron identification. A lead may include recording electrodes spaced around the circumference of the lead to more precisely determine the position of the target neurons. In at least some embodiments, the lead is rotatable so that the stimulation electrodes can be aligned with the target neurons after the neurons have been located using the recording electrodes.

Deep brain stimulation devices and leads are described in the art. See, for instance, U.S. Patent Application Publication No. 2006/0149335 A1 ("Devices and Methods For Brain Stimulation"), U.S. patent application Ser. No. 12/237,888 ("Leads With Non-Circular-Shaped Distal Ends For Brain Stimulation Systems and Methods of Making and Using"), U.S. Patent Application Publication 2007/0150036 A1 ("Stimulator Leads and Methods For Lead Fabrication"), U.S. patent application Ser. No. 12/177,823 ("Lead With Transition and Methods of Manufacture and Use"), U.S. patent application Ser. No. 12/427,935 ("Electrodes For Stimulation Leads and Methods of Manufacture and Use"), U.S. patent application Ser. No. 61/170,037 ("Deep Brain Stimulation Current Steering with Split Electrodes"), U.S. patent application Ser. No. 61/022,953, U.S. patent application Ser. No. 61/316,759, and U.S. patent application Ser. No. 12/356,480. Each of these references is incorporated herein by reference in its respective entirety.

Figure 1:
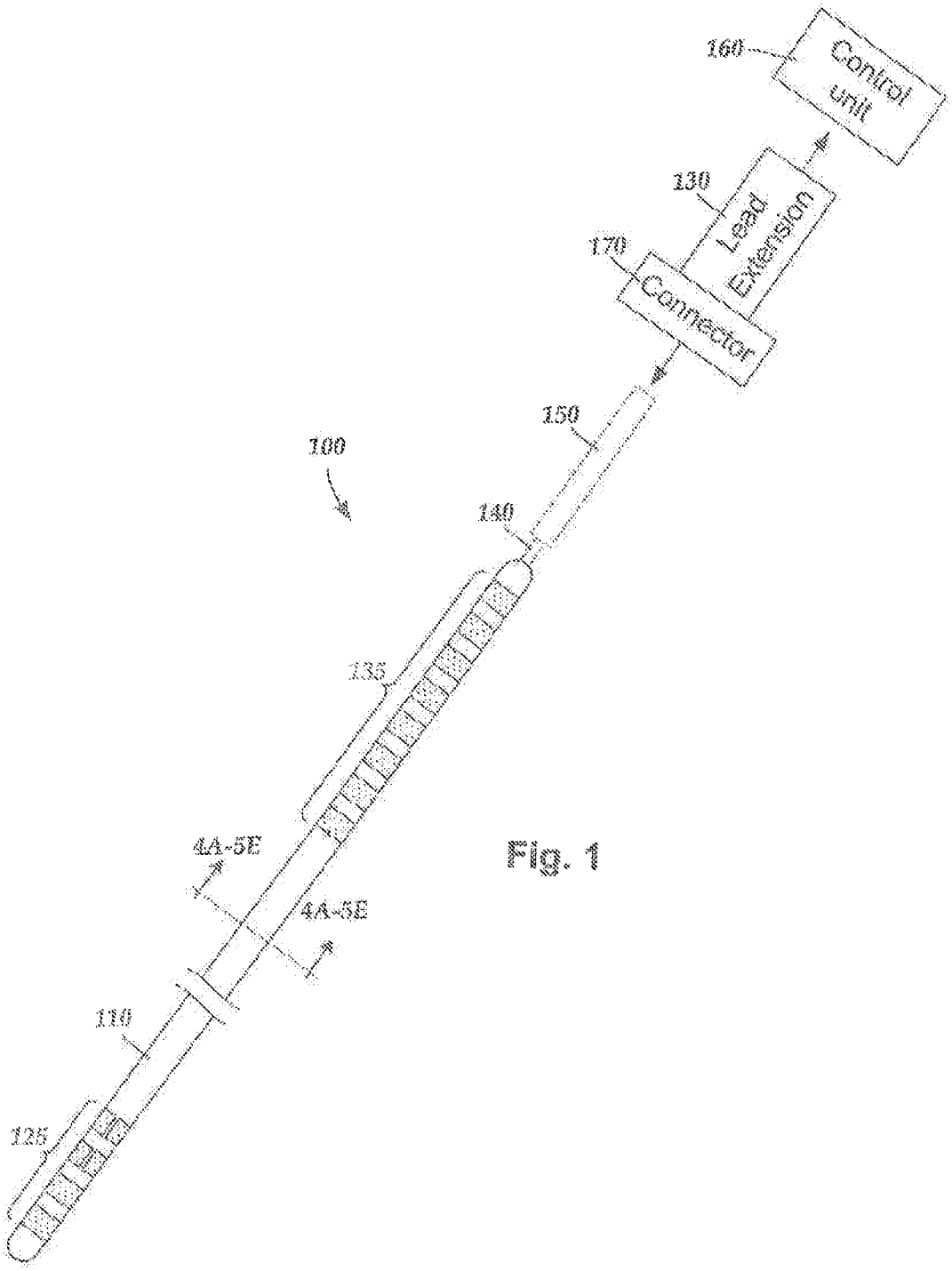
FIG. 1 is a schematic side view of one embodiment of a brain stimulation system that includes a lead, a lead extension, and a control unit, according to the invention.

FIG. 1 illustrates one embodiment of an electrical stimulation system 100 for brain stimulation. The electrical stimulation system 100 includes a lead 110, a plurality of electrodes 125 disposed at least partially about a circumference of the lead 110, a plurality of terminals 135, a lead extension 130 for connection of the electrodes 125 to a control unit 160, and a stylet 140 for assisting in insertion and positioning of the lead 110 in the patient's brain. It may be advantageous to include the lead extensions 130 to prevent having to remove or replace the lead 110 if the proximal end of the lead 110 fails due to fatigue (e.g., from flexing of the patient's neck, or the like).

The stylet 140 can be made of a rigid material. Examples of suitable materials include tungsten, stainless steel, or plastic. The stylet 140 may have a handle 150 to assist insertion into the lead 110, as well as rotation of the stylet 140 and lead 110. The lead extension 130 includes a connector 170 that fits over a proximal end of the lead 110, preferably after removal of the stylet 140.

The control unit 160 is typically an implantable pulse generator that can be implanted into a patient's body, for example, below the patient's clavicle area. The pulse generator can have eight stimulation channels which may be independently programmable to control the magnitude of the current stimulus from each channel. In some cases, the pulse generator may have more than eight stimulation channels (e.g., 16-, 32-, or more stimulation channels). The control unit 160 may have one, two, three, four, or more connector ports, for receiving the plurality of terminals 135 at the proximal end of the lead 110.

In one example of operation, access to the desired stimulation location in the brain can be accomplished by drilling a hole in the patient's skull or cranium with a cranial drill (commonly referred to as a "burr" or "bur"), and coagulating and incising the dura mater, or brain covering. The lead 110 can be inserted into the cranium and brain tissue with the assistance of the stylet 140. The lead 110 can be guided to the target stimulation location within the brain using, for example, a stereotactic frame and a microdrive motor system. In some embodiments, the microdrive motor system can be fully or partially automatic. The microdrive motor system may be configured to perform one or more the following actions (alone or in combination): insert the lead 110, retract the lead 110, or rotate the lead 110.

In some embodiments, measurement devices coupled to the muscles or other tissues stimulated by the target neurons, or a unit responsive to the patient or clinician, can be coupled to the control unit or microdrive motor system. The measurement device, user, or clinician can indicate a response by the target muscles or other tissues to the stimulation or recording electrode(s) to further identify the target neurons and facilitate positioning of the stimulation electrode(s). For example, if the target neurons are directed to a muscle experiencing tremors, a measurement device can be used to observe the muscle and indicate changes in tremor frequency or amplitude in response to stimulation of neurons. Alternatively, the patient or clinician may observe the muscle and provide feedback.

The lead 110 for deep brain stimulation can include stimulation electrodes, recording electrodes, or both. In at least some embodiments, the lead 110 has a cross-sectional diameter of no more than 1.5 mm and may be in the range of 1 to 1.5 mm. In at least some embodiments, the lead 110 is rotatable so that the stimulation electrodes can be aligned with the target neurons after the neurons have been located using the recording electrodes. Stimulation electrodes may be disposed on the circumference of the lead 110 to stimulate the target neurons. Stimulation electrodes may be ring-shaped or segmented.

The lead extension 130 typically couples the electrodes 125 to the control unit 160 (which typically houses a pulse generator that supplies electrical signals to the electrodes 125). Connectors of conventional lead extensions are typically disposed within patient tissue such that the connectors are disposed over the patient's skull and beneath or within the patient's scalp above one of the patient's ear.

It may be desirable for a lead to be flexible. As discussed above, during implantation a distal end of the lead is typically inserted into a burr hole in the patient's scalp and positioned such that the electrodes are disposed at a target stimulation location (e.g., the sub thalamic nucleus, the globus pallidus interna, the ventral intermediate nucleus, or the like). A proximal end of the lead is typically coupled to a connector of a lead extension, disposed between the patient's skull and skin. In which case, the lead may make an approximately 90° bend in proximity to an outer portion of the burr hole through which the distal end of the lead is extended. Consequently, it may be desirable for the lead to be flexible enough to be able to make such a bend.

Figure 2A:
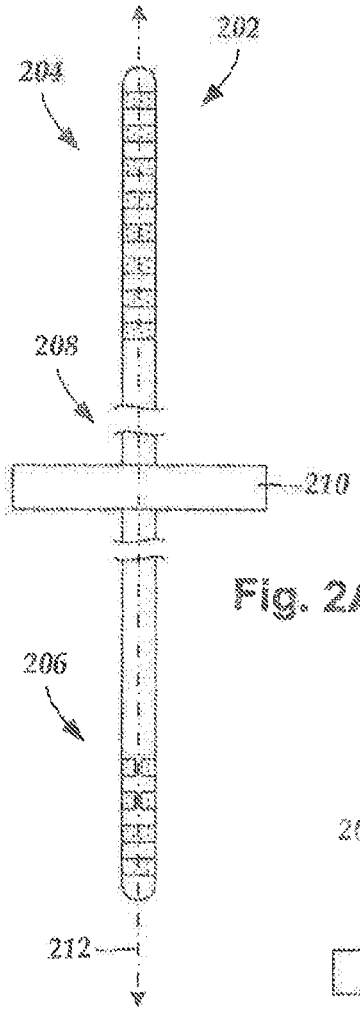
FIG. 2A is a schematic side view of one embodiment of a middle portion of a lead being held in position by a retaining feature.

Bending one portion of the lead, however, might cause a corresponding undesired deflection at another portion of the lead. For example, bending in a proximal portion or a middle portion of the lead may cause a corresponding undesired deflection at a distal end of the lead. Such a deflection may be caused, at least in part, by one or more conductors of the lead being held in tension, while one or more other conductors of the lead are held in compression. FIG. 2A is a schematic side view of one embodiment of a lead 202 having a proximal end 204, a distal end 206, and a middle portion 208. The middle portion 208 of the lead 202 is held in position by a retaining feature 210 (e.g., a burr hole plug or cap, bone cement, one or more mini-plates, or the like). An axis 212 is shown passing through the portion of the lead 202 extending through the retaining feature 210. In FIG. 2A, the lead 202 is shown in a straight configuration, such that the entire lead 202 extends along the axis 212.

Figure 2B:
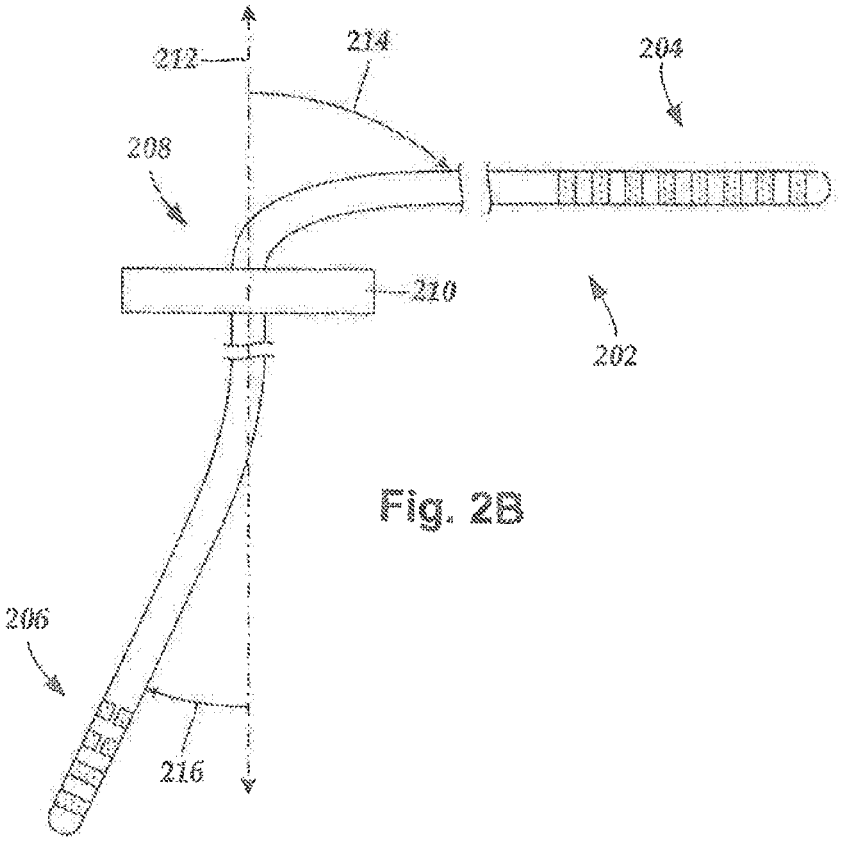
FIG. 2B is a schematic side view of one embodiment of a middle portion of the lead of FIG. 2A being held in position by the retaining feature of FIG. 2A and a proximal end of the lead being bent in a first direction, the bending of the proximal end causing a corresponding deflection of an opposing distal end of the lead in a second direction, opposite from the first direction.

FIG. 2B is a schematic side view of one embodiment of the proximal end 204 of the lead 202 bent in a first direction, away from the axis 212, as shown by arrow 214. As shown in FIG. 2B, bending of the proximal end 204 of the lead 202 in a first direction causes a corresponding deflection of the distal end 206 of the lead 202 in a second direction (opposite to the first direction), away from the axis 212, as shown by arrow 216.

Accordingly, it may be desirable for the lead to include a strain relief that prevents the bending of the lead proximal to a retaining feature (e.g., a burr hole plug or cap, bone cement, one or more mini-plates, or the like) from causing a corresponding deflection of the lead distal to the retaining feature. As herein described, the lead includes a lead body with an elongated multi-lumen conductor guide configured and arranged to improve flexibility from conventional lead bodies and to provide a strain relief that prevents bending of a first end of the lead from causing a corresponding deflection of an opposing end of the lead.

Figure 3:
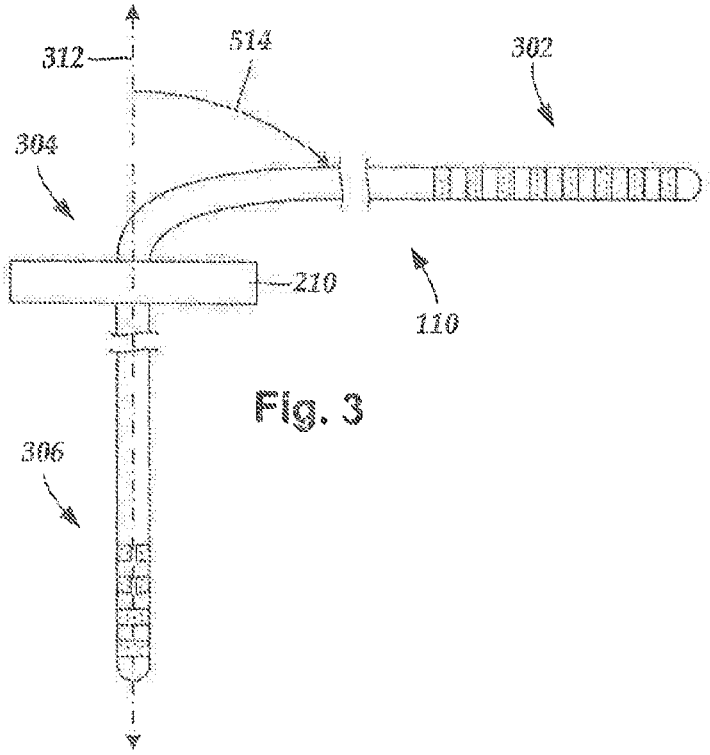
FIG. 3 is a schematic side view of one embodiment of a middle portion of the lead of FIG. 1 held in position by the retaining feature of FIG. 2A and a proximal end of the lead being bent in a first direction, the bending of the proximal end not causing any corresponding deflections of an opposing distal end of the lead, according to the invention.

FIG. 3 is a schematic side view of one embodiment of the lead 110. The lead 110 has a proximal end 302, a middle portion 304, and a distal end 306. The middle portion 304 is held in a relatively stationary position by the retaining feature 210 (e.g., a burr hole plug or cap, bone cement, one or more mini-plates, or the like). An axis 312 is shown passing through the portion of the lead 110 extending through the retaining feature 210.

In FIG. 3, a portion of the lead 110 is shown bent in a first direction from the axis 312, as shown by arrow 514. It will be understood that the bend may occur at any suitable location along the length of the lead 110. For example, in some cases the bend may occur distal to the terminals and proximal to the electrodes. As shown in FIG. 3, bending of a portion of the lead 110 in a first direction does not cause a corresponding deflection of the distal end 306 of the lead 110.

The multi-lumen conductor guide described herein includes multiple conductor lumens arranged about a central stylet lumen. In at least some cases, the conductor lumens are arranged about the central stylet lumen such that there are no other lumens extending along the multi-lumen conductor guide between the central stylet lumen and each of the multiple conductor lumens. The conductor lumens include at least one helical section forming an enclosed pathway around at least a portion of the stylet lumen. In some cases, the conductor lumens are each configured and arranged to receive a single conductor. In other cases, at least one of the conductor lumens is configured and arranged to receive multiple conductors.

Figure 4A:
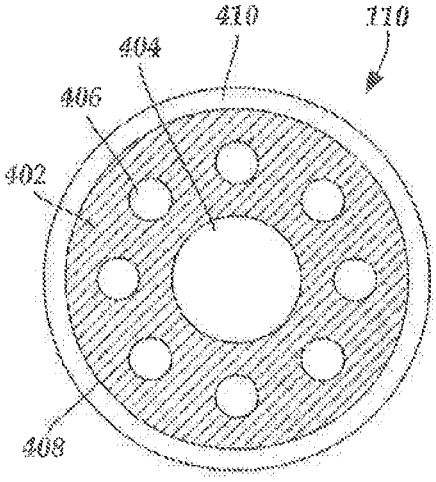
FIG. 4A is a transverse cross-sectional view of one embodiment of the lead of FIG. 1A, the lead including a multi-lumen conductor guide that defines a central stylet lumen and a plurality of conductor lumens arranged around the stylet lumen, according to the invention.

FIG. 4A is a transverse cross-sectional view of one embodiment of the lead 110. The lead 110 includes an elongated multi-lumen conductor guide 402. The multi-lumen conductor guide 402 may extend an entire longitudinal length of the lead 110 from the electrodes 125 to the terminals 135. As shown in FIG. 4A, the multi-lumen conductor guide 402 defines a central stylet lumen 404 and a plurality of conductor lumens, such as conductor lumen 406. The conductor lumens can have any suitable cross-sectional shape (e.g., round, oval, rectangular, triangular, or the like). In preferred embodiments, the conductor lumens have round cross-sectional shapes.

In at least some embodiments, the plurality of conductor lumens 406 are encapsulated by the multi-lumen conductor guide 402 such that the conductor lumens 406 do not extend to an outer surface 408 of the multi-lumen conductor guide 402. In which case, when conductors (420 in FIG. 4B) are disposed in the conductor lumens 406, the conductors are not exposed along the outer surface 408 of the multi-lumen conductor guide 402. The stylet lumen 404 and the plurality of conductor lumens 406 can be arranged in any suitable manner. In preferred embodiments, the conductor lumens 406 are disposed in the multi-lumen conductor guide 402 such that the conductor lumens 406 are peripheral to the stylet lumen 404. In at least some cases, the lead 110 may include one or more outer coatings of material 410 disposed over the outer surface 408 of multi-lumen conductor guide 402.

Figure 4B:
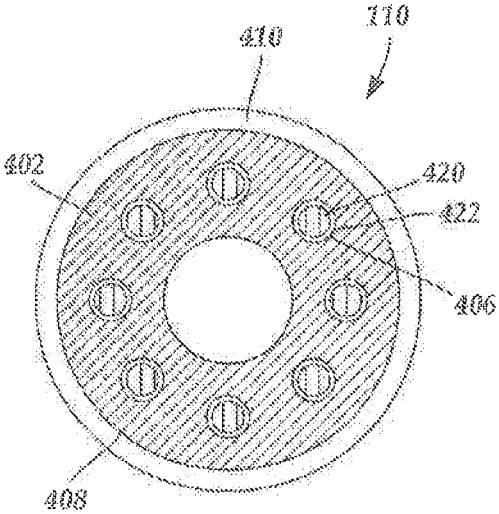
FIG. 4B is a transverse cross-sectional view of one embodiment of conductors disposed in each of a plurality of conductor lumens of the multi-lumen conductor guide of FIG. 4A such that a different single conductor is disposed in each of the conductor lumens, according to the invention.

The stylet lumen 404 is configured and arranged to receive the stylet 140. As discussed above, the stylet 140 can be used for assisting in insertion and positioning of the lead 110 in the patient's brain. The plurality of conductor lumens 406 are configured and arranged to receive conductors, which electrically couple the electrodes 125 to the terminals 135. FIG. 4B is a transverse cross-sectional view of one embodiment of conductors, such as conductor 420, disposed in the conductor lumens 406. In at least some cases, insulation 422 is disposed around the conductors 420 to prevent short-circuiting of the conductors 420.

Figure 5A:
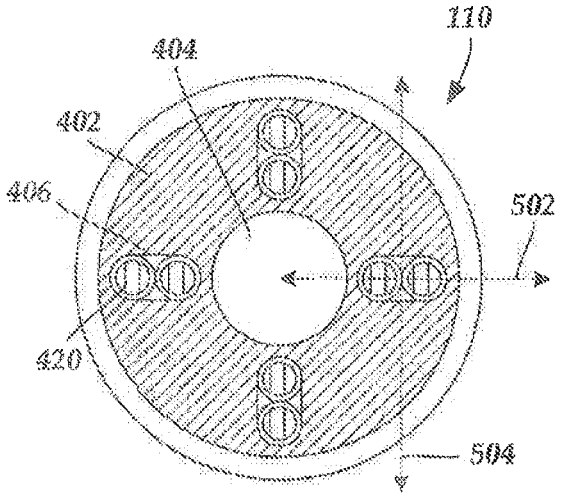
FIG. 5A is a transverse cross-sectional view of another embodiment of the multi-lumen conductor guide of FIG. 4A, the multi-lumen conductor guide defining a plurality of conductor lumens, each of the plurality of conductor lumens receiving a plurality of conductors, according to the invention.
Figure 5B:
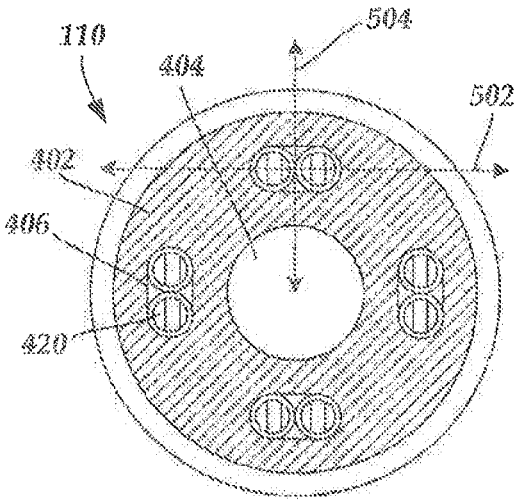
FIG. 5B is a transverse cross-sectional view of yet another embodiment of the multi-lumen conductor guide of FIG. 4A, the multi-lumen conductor guide defining a plurality of conductor lumens, each of the plurality of conductor lumens receiving a plurality of conductors, according to the invention.
Figure 5C:
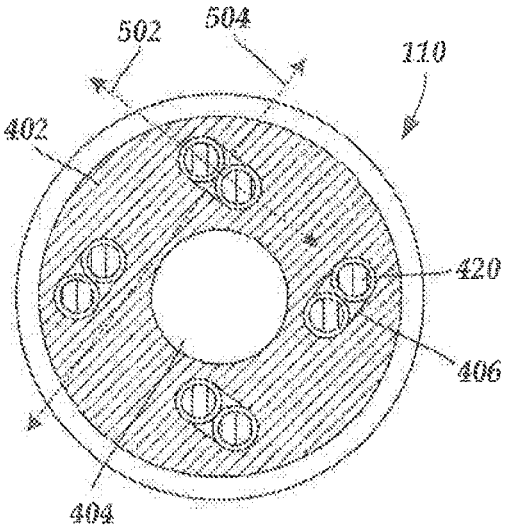
FIG. 5C is a transverse cross-sectional view of another embodiment of the multi-lumen conductor guide of FIG. 4A, the multi-lumen conductor guide defining a plurality of conductor lumens, each of the plurality of conductor lumens receiving a plurality of conductors, according to the invention.

In some cases, two or more conductors 420 can be disposed in one or more of the conductor lumens 406. In at least some cases, the multi-lumen conductor guide 402 defines more than one conductor lumen 406, yet includes fewer conductor lumens 406 than conductors 420. FIG. 5A-5C are transverse cross-sectional views of three other embodiments of the multi-lumen conductor guide 402 defining the stylet lumen 404 and a plurality of conductor lumens, such as conductor lumen 406, where the number of conductor lumens 406 is less than the number of conductors 420. Any suitable such configuration can be implemented. In FIGS. 5A-5C, the multi-lumen conductor guide 402 includes four conductor lumens 406 and eight conductors 420. Each of the conductor lumens shown in FIG. 5A-5C are configured and arranged to receive two conductors 420. In other embodiments, at least one of the conductor lumens 406 can be configured and arranged to receive a different number of conductors than at least one other of the conductor lumens 406.

When the conductor lumens 406 are configured and arranged to receive a plurality of conductors, the conductor lumens 406 can be arranged in any suitable configuration. In FIGS. 5A-5C, the conductor lumens 406 each have a major axis 502 and a minor axis 504 that is perpendicular to the major axis 502. In FIG. 5A, the conductor lumens 406 are configured and arranged such that the major axes 502 of the conductor lumens 406 extends radially outward from the stylet lumen 404. In FIG. 5B, the conductor lumens 406 are configured and arranged such that the minor axes 504 of the conductor lumens 406 extends radially outward from the stylet lumen 404. In FIG. 5C, the conductor lumens 406 are configured and arranged such that neither the major axes 502 nor the minor axis 504 of the conductor lumens 406 extend radially outward from the stylet lumen 404.

Figure 6A:
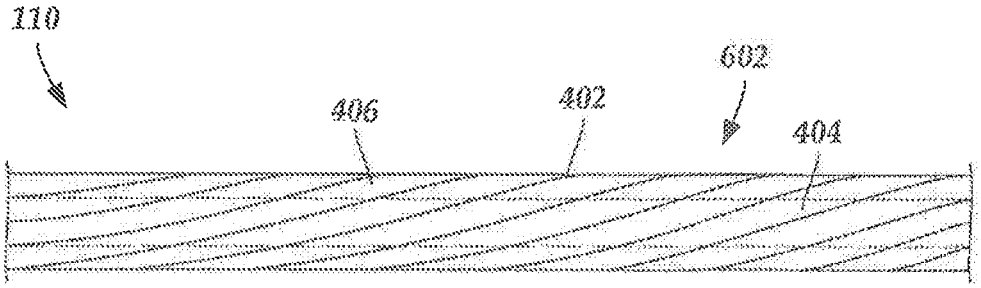
FIG. 6A is a schematic side view of one embodiment of a helical section of the multi-lumen conductor guide of FIG. 4A, the helical section defining a plurality of conductor lumens each defining a clockwise helical pathway around at least a portion of a stylet lumen, according to the invention.
Figure 6B:
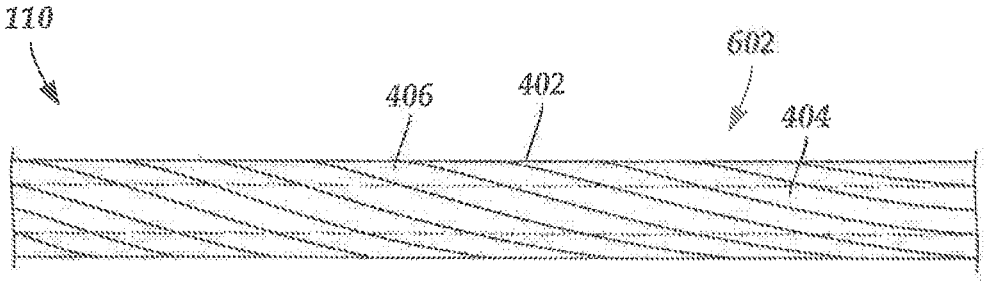
FIG. 6B is a schematic side view of another embodiment of a helical section of the multi-lumen conductor guide of FIG. 4A, the helical section defining a plurality of conductor lumens each defining a counter-clockwise helical pathway around at least a portion of a stylet lumen, according to the invention.

FIGS. 6A and 6B are schematic side views of two embodiments of a helical section 602 of the multi-lumen conductor guide 402. The helical section 602 can extend an entire length of the multi-lumen conductor guide 402, or one or more portions thereof. The multi-lumen conductor guide 402 defines a plurality of conductor lumens, such as conductor lumen 406, twisted such that the individual conductor lumens 406 form helical pathways around the stylet lumen 404. The conductor lumens 406 can extend in either clockwise or counter-clockwise directions. In FIG. 6A, the conductor lumens 406 are shown extending in a clockwise direction around to the stylet lumen 404 (e.g., the conductor lumens 406 wrap around the stylet lumen in a clockwise direction when the multi-lumen conductor guide 402 is viewed from the distal end). In FIG. 6B, the conductor lumens 406 are shown extending in a counter-clockwise direction around to the stylet lumen 404 (e.g., the conductor lumens 406 wrap around the stylet lumen in a counter-clockwise direction when the multi-lumen conductor guide 402 is viewed from the distal end). It should be understood that the twisted lead embodiments of FIGS. 6A and 6B may have transverse, cross-sections that are shown in FIGS. 4A, 4B, 5A, 5B and 5C.

The conductor lumens 406 of the helical section 602 can be any suitable pitch. The pitch can be either constant or variable. In some cases, the pitch may be no less than 0.04 turns (i.e., 0.04 revolutions around a circumference of the stylet lumen 404) per cm. In some cases, the pitch may be no less than 0.1 turns per cm. In some cases, the pitch may be no less than 0.2 turns per cm. In some cases, the pitch may be no less than 0.25 turns per cm. In some cases, the pitch may be no greater than 0.8 turns per cm.

In some cases, the pitch may be no less than 0.04 turns per cm and no greater than 0.8 turns per cm. In some cases, the pitch may be no less than 0.1 turns per cm and no greater than 0.6 turns per cm. In some cases, the pitch may be no less than 0.1 turns per cm and no greater than 0.4 turns per cm. In some cases, the pitch may be no less than 0.2 turns per cm and no greater than 0.4 turns per cm. In some cases, the pitch may be approximately 0.3 turns per cm.

In some cases, for a 40 cm section of the multi-lumen conductor guide 402, each conductor lumen 406 of the helical section 602 forms at least 2, 3, 4, or 5 turns. In some cases, for a 40 cm section of the multi-lumen conductor guide 402, each conductor lumen 406 of the helical section 602 forms no more than 25 turns.

In some cases, for a 40 cm section of the multi-lumen conductor guide 402, each conductor lumen 406 of the helical section 602 forms no less than 2 turns and no more than 15 turns. In some cases, for a 40 cm section of the multi-lumen conductor guide 402, each conductor lumen 406 of the helical section 602 forms no less than 3 turns and no more than 15 turns. In some cases, for a 40 cm section of the multi-lumen conductor guide 402, each conductor lumen 406 of the helical section 602 forms no less than 4 turns and no more than 15 turns. In some cases, for a 40 cm section of the multi-lumen conductor guide 402, each conductor lumen 406 of the helical section 602 forms no less than 5 turns and no more than 15 turns.

The conductor lumens 406 of the helical section 602 can be configured into any suitable arrangement (see e.g., FIGS. 4A-5C). The helical section 602 may include a single layer of conductor lumens 406 disposed over the stylet lumen 404. The conductor lumens 406 may be disposed over a single stylet lumen 404. In some cases, a single layer of conductor lumens 406 is disposed over a single stylet lumen 404.

In some cases, the helical section 602 extends along an entire length of the lead 110 between the electrodes (125 in FIG. 1) and the terminals (135 in FIG. 1). In other cases, the helical section 602 extends along one or more discrete sections of the lead 110. When the helical section 602 extends along one or more discrete sections of the lead 110, the discrete helical section 602 can be any suitable length. In some cases, the discrete helical section 602 is at least 1 cm, 2 cm, 3 cm, 4 cm, 5 cm, 6 cm, 7 cm, 8 cm, 9 cm, 10 cm, 15 cm, 20 cm, 25 cm, 30 cm, or longer.

Figure 7A:
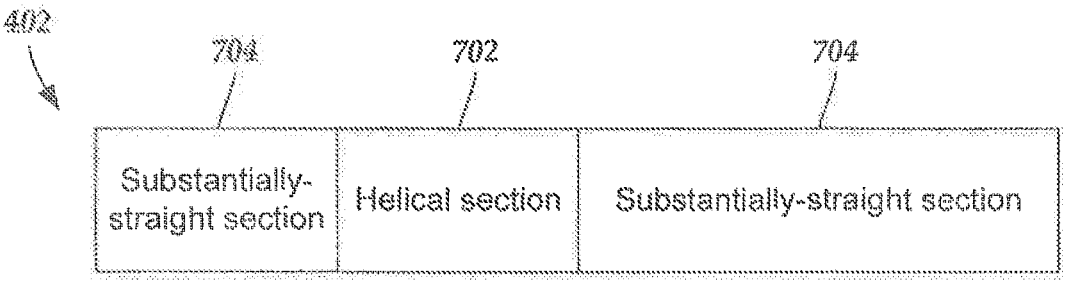
FIG. 7A is a schematic side view of one embodiment of a portion of the multi-lumen conductor guide of FIG. 4A, the portion of the multi-lumen conductor guide defining the discrete helical section of either FIG. 6A or FIG. 6B, according to the invention.

Turning to FIG. 7A, when the helical section 602 extends along a discrete section of the multi-lumen conductor guide 402, the discrete helical section 602 can be disposed at any suitable location along the length of the lead 110. In some cases, the discrete helical section 110 may abut the electrodes (125 in FIG. 1), the terminals (135 in FIG. 1), or both. In other cases, the discrete helical section 602 can be disposed somewhere along the length of the lead 110 between the electrodes (125 in FIG. 1) and the terminals (135 in FIG. 1). When the discrete helical section 602 is disposed somewhere along the length of the lead 110 between the electrodes (125 in FIG. 1) and the terminals (135 in FIG. 1), the remaining portions of the conductor lumens 406 can be arranged into one or more other configurations, such as a substantially-straight configuration (e.g., the conductor lumens 406 extend less than one revolution about a circumference of the stylet lumen 404 along a 20 cm length of the multi-lumen conductor guide 402).

FIG. 7A is a schematic side view of one embodiment of a portion of the multi-lumen conductor guide 402. The portion of the multi-lumen conductor guide 402 defines a discrete helical section 702 where each of a plurality of conductor lumens defines a helical pathway around at least a portion of a circumference of a stylet lumen. In FIG. 7A, substantially-straight sections 704 of the conductor lumens extend along the multi-lumen conductor guide 402 on either end of the discrete helical section 702. The helical section 702 and the flanking substantially-straight sections 704 can be any suitable lengths relative to one another.

Figure 7B:
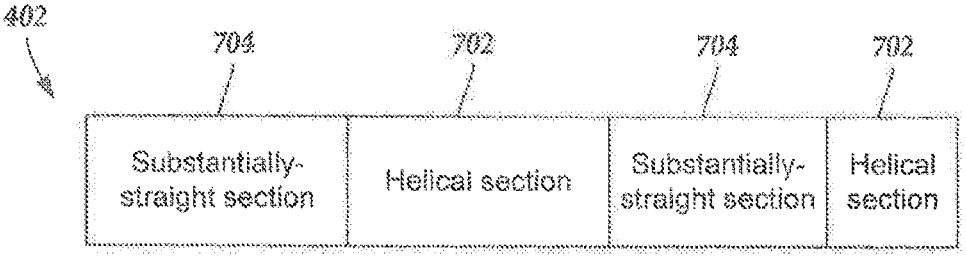
FIG. 7B is a schematic side view of one embodiment of a portion of the multi-lumen conductor guide of FIG. 4A, the portion of the multi-lumen conductor guide defining a plurality of the discrete helical sections of either FIG. 6A or FIG. 6B each separated from one another by substantially-straight sections, according to the invention.

Turning to FIG. 7B, in some cases the multi-lumen conductor guide includes a plurality of helical sections. When the lead includes a plurality of helical sections, the conductor lumens of the helical sections can extend around the stylet lumen in either: a clockwise direction; a counter-clockwise direction; or a combination of both, where at least one conductor lumen extends clockwise and at least one conductor lumen that extends counter-clockwise around the circumference of the stylet lumen. In some cases, when the multi-lumen conductor guide includes a plurality of helical sections, the helical sections each have equal lengths. In other cases, when the lead includes a plurality of helical sections, at least one of the helical sections has a length that is different from at least one other of the plurality of helical sections.

FIG. 7B is a schematic side view of one embodiment of a portion of the multi-lumen conductor guide 402. The portion of the multi-lumen conductor guide 402 defines a plurality of the discrete helical sections 702. In FIG. 7B, a substantially-straight section 704 is disposed between the discrete helical sections 702.

Figure 7C:
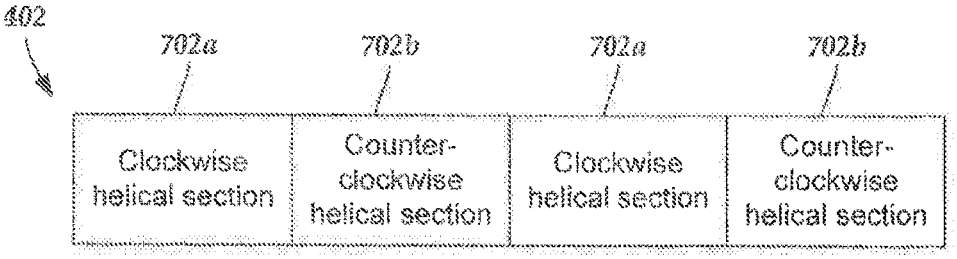
FIG. 7C is a schematic side view of one embodiment of a portion of the multi-lumen conductor guide of FIG. 4A, the portion of the multi-lumen conductor guide defining a plurality of the discrete helical sections of FIG. 6A and FIG. 6B abutting one another, according to the invention.

Turning to FIG. 7C, in some cases the multi-lumen conductor includes two abutting discrete helical sections with conductors winding in opposite directions. FIG. 7C is a schematic side view of one embodiment of a portion of the multi-lumen conductor guide 402. The portion of the multi-lumen conductor guide 402 defines a plurality of the discrete helical sections abutting one another. At least one of the helical sections 702a includes conductor lumens arranged in a clockwise configuration, and at least one of the helical sections 702b includes conductor lumens arranged in a counter-clockwise configuration.

Figure 7D:
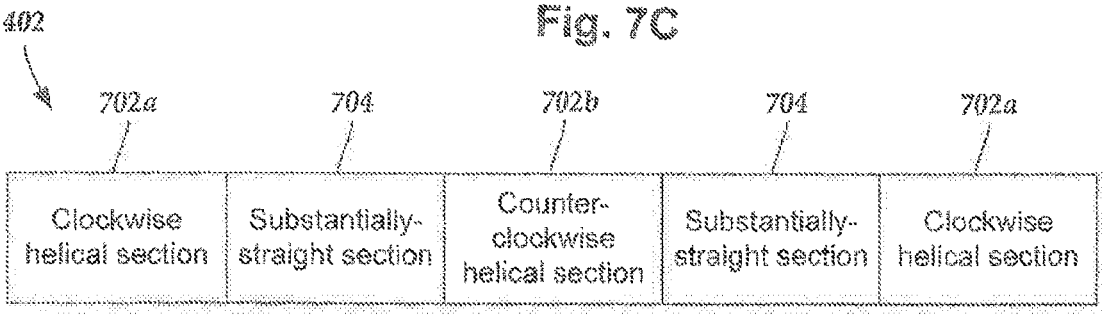
FIG. 7D is a schematic side view of one embodiment of a portion of the multi-lumen conductor guide of FIG. 4A, the portion of the multi-lumen conductor guide defining a plurality of the discrete helical sections of FIG. 6A and FIG. 6B with alternating winding geometries, the helical sections each separated from one another by substantially-straight sections, according to the invention.

Turning to FIG. 7D, in some cases the multi-lumen conductor includes multiple discrete helical sections with conductors winding in opposite directions, where the discrete helical sections are separated from one another by substantially-straight sections. FIG. 7D is a schematic side view of one embodiment of a portion of the multi-lumen conductor guide 402. The portion of the multi-lumen conductor guide 402 defines a plurality of discrete helical sections 702a and 702b. The helical sections alternate between helical sections 702a having conductor lumens arranged in a clockwise configuration, and helical sections 702b having conductor lumens arranged in a counter-clockwise configuration. A substantially-straight section 704 separates each of the alternating helical sections 702a and 702b from one another.

Figure 7E:
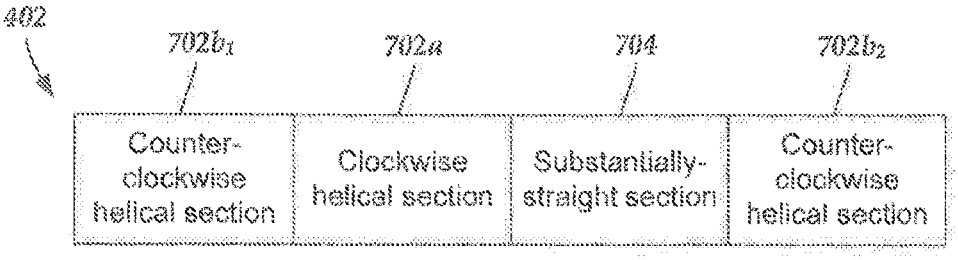
FIG. 7E is a schematic side view of one embodiment of a portion of the multi-lumen conductor guide of FIG. 4A, the portion of the multi-lumen conductor guide defining a plurality of the discrete helical sections of FIG. 6A and FIG. 6B, some of the helical sections abutting one another and some of the helical sections separated from one another by a substantially-straight section, according to the invention.

FIG. 7E is a schematic side view of one embodiment of a portion of the multi-lumen conductor guide 402. The portion of the multi-lumen conductor guide 402 defines a plurality of discrete helical sections. At least some of the helical sections, such as helical sections 702a and 702$b_1$, abut one another. At least some of the helical sections, such as helical sections 702a and 702$b_2$, are separated from one another by a substantially-straight section 704. Additionally, at least one of the helical sections, such as helical section 702a includes conductor lumens arranged in a clockwise configuration, and at least one of the helical sections, such as helical sections 702$b_1$ and 702$b_2$, include conductor lumens arranged in a counter-clockwise configuration.

The multi-lumen conductor guide 402 can be formed as a single-piece component or as a multi-piece component. The multi-lumen conductor guide 402 can be formed from any suitable material(s). For example, the multi-lumen conductor guide 402 can be formed from one or more thermoset polymers, thermoplastic polymers (e.g., polyurethane, or the like), silicone, or the like or combinations thereof.

The multi-lumen conductor guide 402 can be formed in any suitable manner. For example, the multi-lumen conductor guide 402 can be extruded. In some cases, the multi-lumen conductor guide 402 can be twisted as the multi-lumen conductor guide 402 is being extruded, or after extrusion.

The multi-lumen conductor guide 402 can be formed such that the conductor lumens are in substantially-straight configurations. In some cases, the multi-lumen conductor guide 402 (or one or more portions thereof) with the substantially-straight conductor-lumen configurations can be twisted, as desired, to form one or more helical sections. Once the twisting is complete, the twisted multi-lumen conductor guide can be heated to set the helical section(s). In other cases, the multi-lumen conductor guide can be heated prior to twisting. In yet other cases, the multi-lumen conductor guide can be heated while being twisted. The heating can be performed using at least one of: one or more transverse heating elements which heat one or more particular portions of the multi-lumen conductor guide at a time, or an elongated heating element that heats the entire multi-lumen conductor guide at once. In some cases, the lead can be heated from the inside out, for example, by using one or more heating elements disposed in the stylet lumen.

In some cases, the conductors can be disposed in the conductor lumens prior to heating. In other cases, the conductor lumens can be empty during heating. In preferred embodiments, one or more mandrels are disposed in at least some of the conductor lumens. It may be advantageous to dispose mandrels in the conductor lumens prior to heating of the multi-lumen conductor guide to prevent the conductor lumens from collapsing during heating.

In at least some cases, a different mandrel is disposed in each of the conductor lumens during the heating process and then removed for insertion of the conductors. Optionally, a mandrel can be disposed in the stylet lumen. The mandrels disposed in the conductor lumens can have any suitable diameter. In at least some cases, the mandrels have diameters that are smaller than diameters of the conductor lumens, yet larger than diameters of the conductors. It may be advantageous to use mandrels with diameters that are smaller than diameters of the conductor lumens, yet larger than diameters of the conductors so that, during the heating process, the conductor lumens do not shrink to a size that prevents (or makes difficult) insertion of the conductors into the conductor lumens after the multi-lumen conductor guide is twisted and heated, and the mandrels are removed.

The above specification, examples, and data provide a description of the manufacture and use of the composition of the invention. Since many embodiments of the invention can be made without departing from the spirit and scope of the invention, the invention also resides in the claims hereinafter appended.

What is claimed as new and desired to be protected by Letters Patent of the United States is:

[1. A lead for providing deep brain stimulation the lead comprising:

a lead body having a distal end, a proximal end, and a longitudinal length, the lead body comprising a multi-lumen conductor guide having an outer surface and defining a central stylet lumen configured and arranged for receiving a stylet and a plurality of conductor lumens disposed around the central stylet lumen in a ring, each conductor lumen configured and arranged to receive at least one conductor, wherein the plurality of conductor lumens are completely inset from the outer surface of the multi-lumen conductor guide, wherein at least a portion of the multi-lumen conductor guide is twisted such that the multi-lumen conductor guide forms at least a first helical section and a second helical section where each of the plurality of conductor lumens forms a helical pathway around the stylet lumen, wherein each of the helical pathways of the first and second helical sections has a pitch that is no less than 0.04 turns per centimeter, wherein the multi-lumen conductor guide further forms a first straight section disposed between the first helical section and the second helical section;

a plurality of electrodes disposed on the distal end of the lead body;

a plurality of lead terminals disposed on the proximal end of the lead body; and a plurality of conductors electrically coupling the plurality of electrodes to the plurality of lead terminals, wherein the plurality of conductors extend along the longitudinal length of the leady body within the plurality of conductor lumens, wherein the multi-lumen conductor guide extends the entire longitudinal length of the lead body from the electrodes to the terminals.]

[2. The lead of claim 1, wherein each of the plurality of conductor lumens is configured and arranged to receive a different single conductor of the plurality of conductors.]

[3. The lead of claim 1, wherein each of the plurality of conductor lumens is configured and arranged to receive a plurality of conductors of the plurality of conductors.]

[4. The lead of claim 1, wherein the first helical section and the second helical section are twisted in opposite directions from one another along the longitudinal length of the lead body.]

[5. The lead of claim 1, wherein the first helical section has a constant pitch.]

[6. The lead of claim 1, wherein the first helical section has a variable pitch.]

[7. An electrical stimulation system comprising:

the lead of claim 1; and a control unit coupleable to lead, the control unit configured and arranged for providing stimulation to the plurality of electrodes of the lead.]

[8. A method for manufacturing the lead of claim 1, the method comprising:

forming the multi-lumen conductor guide defining the central stylet lumen and the plurality of conductor lumens arranged around the stylet lumen; and twisting the multi-lumen conductor guide to form the first helical section wherein the first helical section has the pitch that is no less than 0.04 turns per centimeter.]

[9. The method of claim 8, further comprising applying heat to the multi-lumen conductor guide to set the first helical section.]

[10. The method of claim 9, further comprising inserting at least one of the plurality of conductors into at least one of the plurality of conductor lumens.]

[11. The method of claim 10, further comprising inserting at least one mandrel into each of the plurality of conductor lumens prior to applying heat to the multi-lumen conductor guide.]

[12. The method of claim 11, further comprising removing the at least one mandrel from each of the plurality of conductor lumens prior to inserting the at least one conductor into each of the plurality of conductor lumens.]

[13. The method of claim 8, wherein twisting the multi-lumen conductor guide comprises twisting the multi-lumen conductor guide to form helical pathways each having a pitch that is no greater than 0.8 turns per centimeter.]

[14. The method of claim 8, wherein forming an elongated multi-lumen conductor guide comprising extruding the multi-lumen conductor guide and wherein twisting the multi-lumen conductor guide comprises twisting the multi-lumen conductor guide while extruding the multi-lumen conductor guide.]

[15. A lead for providing deep brain stimulation, the lead comprising:

a lead body having a distal end, a proximal end, and a longitudinal length, the lead body comprising a multi-lumen conductor guide having an outer surface and defining a central stylet lumen configured and arranged for receiving a stylet and a plurality of conductor lumens disposed around the central stylet lumen in a ring, each conductor lumen configured and arranged to receive at least one conductor, wherein the plurality of conductor lumens are completely inset from the outer surface of the multi-lumen conductor guide, wherein at least a portion of the multi-lumen conductor guide is twisted such that the multi-lumen conductor guide forms at least a first helical section and a second helical section where each of the plurality of conductor lumens forms a helical pathway around the stylet lumen, wherein each of the helical pathways of the first and second helical sections has a pitch that is no less than 0.04 turns per centimeter, wherein the first and second helical sections are axially separate from each other and the first helical section and the second helical section are twisted in opposite directions from one another along the longitudinal length of the lead body;

a plurality of electrodes disposed on the distal end of the lead body;

a plurality of lead terminals disposed on the proximal end of the lead body; and a plurality of conductors electrically coupling the plurality of electrodes to the plurality of lead terminals, wherein the plurality of conductors extend along the longitudinal length of the leady body within the plurality of conductor lumens, wherein the multi-lumen conductor guide extends the entire longitudinal length of the lead body from the electrodes to the terminals.]

[16. The lead of claim 15, wherein each of the plurality of conductor lumens is configured and arranged to receive a different single conductor of the plurality of conductors.]

[17. The lead of claim 15, wherein each of the plurality of conductor lumens is configured and arranged to receive a plurality of conductors of the plurality of conductors.]

[18. The lead of claim 15, wherein the first helical section has a constant pitch.]

[19. The lead of claim 15, wherein the first helical section has a variable pitch.]

[20. An electrical stimulation system comprising:

the lead of claim 15; and a control unit coupleable to lead, the control unit configured and arranged for providing stimulation to the plurality of electrodes of the lead.]

*21. A lead, comprising:*

*a lead body having a distal end, a proximal end, and a longitudinal length, the lead body comprising a multi-lumen conductor guide having an outer surface and defining a central stylet lumen and a plurality of conductor lumens extending along the multi-lumen conductor guide and disposed around the central stylet lumen in a ring, each conductor lumen configured and arranged to receive at least one conductor, wherein the plurality of conductor lumens are completely inset from the outer surface of the multi-lumen conductor guide, wherein at least a portion of the multi-lumen conductor guide is twisted such that the multi-lumen conductor guide forms at least one helical section where each of the plurality of conductor lumens forms a helical pathway along the at least one helical section of the multi-lumen conductor guide, wherein each of the helical pathways of the at least one helical section has a pitch that is no less than 0.04 turns per centimeter, the lead body further comprising at least one outer coating of material disposed over the outer surface of the multi-lumen conductor guide;*

*a plurality of electrodes disposed on the distal end of the lead body;*

*a plurality of lead terminals disposed on the proximal end of the lead body; and*

*a plurality of conductors electrically coupling the plurality of electrodes to the plurality of lead terminals, wherein the plurality of conductors extend along the longitudinal length of the lead body within the plurality of conductor lumens, wherein the multi-lumen conductor guide extends the entire longitudinal length of the lead body from the electrodes to the terminals.*

*22. The lead of claim 21, wherein the multi-lumen conductor guide further forms at least one straight section adjacent at least one of the at least one helical section.*

*23. The lead of claim 21, wherein at least one of the at least one helical section has a pitch that is no more than 0.8 turns per centimeter.*

*24. The lead of claim 21, wherein each of the at least one helical section has a pitch that is no more than 0.8 turns per centimeter.*

*25. An electrical stimulation system comprising:*

*the lead of claim 21; and*

*a control unit coupleable to lead, the control unit configured and arranged for providing stimulation to the plurality of electrodes of the lead.*

*26. A method for manufacturing the lead of claim 21, the method comprising:*

*forming the multi-lumen conductor guide defining the plurality of conductor lumens; and*

*twisting the multi-lumen conductor guide to form the at least one helical section.*

*27. The method of claim 26, further comprising applying heat to the multi-lumen conductor guide to set the at least one helical section.*

*28. The method of claim 26, wherein twisting the multi-lumen conductor guide comprises twisting the multi-lumen conductor guide to form helical pathways each having a pitch that is no more than 0.8 turns per centimeter.*

*29. The method of claim 26, wherein forming an elongated multi-lumen conductor guide comprising extruding the multi-lumen conductor guide and wherein twisting the multi-lumen conductor guide comprises twisting the multi-lumen conductor guide while extruding the multi-lumen conductor guide.*

*30. A lead, comprising:*

*a lead body having a distal end, a proximal end, and a longitudinal length, the lead body comprising a multi-lumen conductor guide having an outer surface and defining a central stylet lumen and a plurality of conductor lumens extending along the multi-lumen conductor guide and disposed around the central stylet lumen in a ring, each conductor lumen configured and arranged to receive at least one conductor, wherein the plurality of conductor lumens are completely inset from the outer surface of the multi-lumen conductor guide, wherein at least a portion of the multi-lumen conductor guide is twisted such that the multi-lumen conductor guide comprises a first straight section, a helical section where each of the plurality of conductor lumens forms a helical pathway along the helical section of the multi-lumen conductor guide, and a second straight section, wherein the helical section is disposed between the first straight section and the second straight section and has a pitch that is no less than 0.04 turns per centimeter;*

*a plurality of electrodes disposed on the distal end of the lead body;*

*a plurality of lead terminals disposed on the proximal end of the lead body; and*

*a plurality of conductors electrically coupling the plurality of electrodes to the plurality of lead terminals, wherein the plurality of conductors extend along the longitudinal length of the lead body within the plurality of conductor lumens, wherein the multi-lumen conductor guide extends at least from the electrodes to the terminals.*

*31. The lead of claim 30, wherein the helical section has a pitch that is no more than 0.8 turns per centimeter.*

*32. The lead of claim 30, wherein the helical section has a constant pitch.*

*33. The lead of claim 30, wherein the helical section has a variable pitch.*

*34. The lead of claim 30, wherein each of the plurality of conductor lumens is configured and arranged to receive a different single conductor of the plurality of conductors.*

*35. The lead of claim 30, wherein each of the plurality of conductor lumens is configured and arranged to receive a plurality of conductors of the plurality of conductors.*

*36. A method for manufacturing the lead of claim 30, the method comprising:*

*forming the multi-lumen conductor guide defining the plurality of conductor lumens; and*

*twisting a portion of the multi-lumen conductor guide to form the helical section.*

*37. The method of claim 36, wherein the helical section has the pitch that is no more than 0.8 turns per centimeter.*

*38. The method of claim 36, further comprising applying heat to the multi-lumen conductor guide to set the helical section.*

*39. The method of claim 36, wherein twisting the multi-lumen conductor guide comprises twisting the multi-lumen conductor guide to form helical pathways each having a pitch that is no greater than 0.08 turns per centimeter.*

*40. The method of claim 36, wherein forming an elongated multi-lumen conductor guide comprising extruding the multi-lumen conductor guide and wherein twisting the multi-lumen conductor guide comprises twisting the multi-lumen conductor guide while extruding the multi-lumen conductor guide.*

* * * * *